United States Patent [19]
Dannenbaum

[11] Patent Number: 5,727,945
[45] Date of Patent: Mar. 17, 1998

[54] IMPREGNATED BARRIER AND METHOD OF ASSISTING BONE OR TISSUE REGENERATION

[76] Inventor: Richard M. Dannenbaum, 8 North Union Ave., Margate, N.J. 08402

[21] Appl. No.: 703,260

[22] Filed: Aug. 26, 1996

[51] Int. Cl.$^6$ ............................................. A61C 5/00
[52] U.S. Cl. ........................................... 433/215; 424/435
[58] Field of Search ........................ 433/215; 424/426, 424/435, 444; 606/151, 154, 155, 156

[56] References Cited

U.S. PATENT DOCUMENTS

| | | | |
|---|---|---|---|
| 3,919,773 | 11/1975 | Freeman | 433/201.1 |
| 4,186,448 | 2/1980 | Brekke | 128/92 B |
| 4,863,974 | 9/1989 | Mallouk et al. | 521/85 |
| 5,032,445 | 7/1991 | Scantlebury et al. | 433/215 |
| 5,059,123 | 10/1991 | Jernberg | 433/215 |
| 5,093,179 | 3/1992 | Scantlebury et al. | 433/215 |
| 5,171,148 | 12/1992 | Wasserman et al. | 433/215 |
| 5,197,882 | 3/1993 | Jernberg | 433/215 |
| 5,360,341 | 11/1994 | Abramowitz | 433/215 |
| 5,366,507 | 11/1994 | Sottosanti | 424/424 |
| 5,368,859 | 11/1994 | Dunn et al. | 424/426 |
| 5,425,639 | 6/1995 | Anders | 433/169 |
| 5,447,725 | 9/1995 | Damani et al. | 424/435 |

OTHER PUBLICATIONS

Patient Information on Guided Tissue Regeneration: Guidor® Bioresorbable Matrix Barrier, John O. Butler Company, 1993.

Capset™ Calcium Sulfate Bone Graft Barrier, Lifecore Biomedical, Inc., 1996.

Gore Regenerative Technologies: Product Configurations, W.L. Gore Gore & Associates, 1994.

*Primary Examiner*—John J. Wilson
*Attorney, Agent, or Firm*—Panitch Schwarze Jacobs & Nadel, P.C.

[57] ABSTRACT

A bioresorbable device for use in regeneration of at bone and/or tissue in either a bone void or a tissue deficiency is provided. A primary embodiment is a bioresorbable periodontal barrier for use in regeneration of a periodontal bone and/or tissue in either a gingival pocket adjacent to a patient's tooth or an edentulous area. The bioresorbable periodontal barrier includes a formable membrane constructed of a bioresorbable material and having a microstructure configured for aiding and guiding periodontal tissue growth, and a bioresorbable hardening agent pre-impregnated in the membrane. The membrane is formed to a desired shape and the hardening agent is activated to harden so that the membrane retains the desired shape. A method of assisting bone and/or tissue regeneration in either a bone void or tissue deficiency is also provided. A primary embodiment is a method of assisting and guiding periodontal bone and/or tissue regeneration in a gingival pocket adjacent to a patient's tooth or in an edentulous area. The method includes implanting a barrier over the gingival pocket, forming the membrane into a desired shape which covers the gingival pocket, and allowing the periodontal bone and/or the periodontal tissue to regenerate into the enclosed gingival pocket.

11 Claims, 3 Drawing Sheets

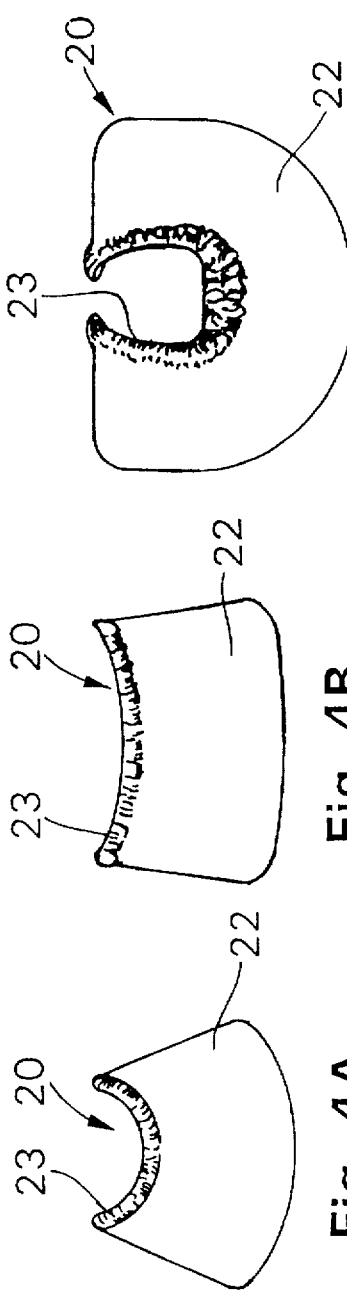
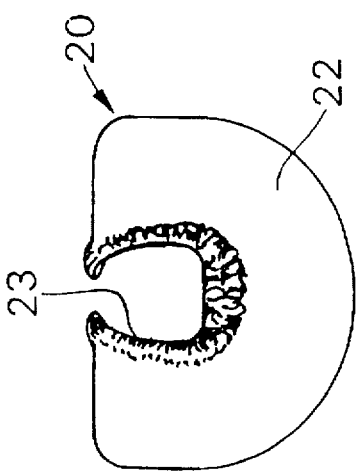
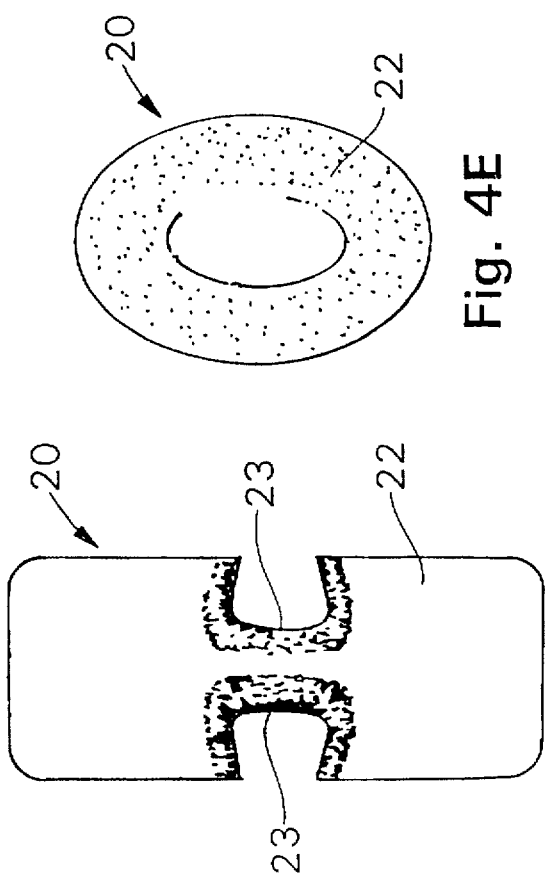
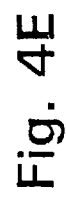

IMPREGNATED BARRIER AND METHOD OF ASSISTING BONE OR TISSUE REGENERATION

FIELD OF THE INVENTION

The present invention relates to barriers for bone or tissue Regeneration, and more particularly, to bioresorbable periodontal barriers for assisting periodontal bone or tissue regeneration.

BACKGROUND OF THE INVENTION

One of the major concerns of dentistry is the treatment of periodontal diseases. Periodontitis is an ordinarily slow developing disease that is caused by bacteria in the mouth. The bacteria forms a sticky and almost invisible plaque on tooth surfaces and the plaque in turn causes an inflammatory process to occur in the gum tissue. If the plaque is not removed by effective brushing and flossing, the plaque may invade the periodontal tissue or ligament that connects teeth to the supporting bone, with subsequent destruction of the fibers and the bone itself. It is this condition which is referred to as periodontitis. Once the disease is established in the vicinity of a tooth, it spreads along the root of the tooth and destroys the support for the tooth, forming deep pockets. Eventually, the tooth itself may be lost.

A variety of methods of treating periodontal diseases and devices used in such treatments are well known in the prior art. In particular, it is known to surgically implant a barrier about the site of a defect in the periodontal structure to facilitate regeneration of tissue infected by or lost to periodontitis. Such barriers are typically implanted about the site of a tissue defect to form a surface over which the gingiva is sutured to prevent the gingiva from entering the defect site, and thus hinder bone and tissue regeneration. The barrier forms an enclosed pocket into which the periodontal bone and tissue regenerates. In earlier treatment procedures, a second surgical procedure to remove the barrier was required after the bone and/or tissue was given sufficient time to regenerate. More recently, "bioresorbable" or body absorbable barriers have been developed which do not require a second removal operation, but, instead, disintegrate and are absorbed by the body after a sufficient time has passed for periodontal bone and tissue regeneration.

The prior non-resorbable barriers often have more structural integrity than the resorbable barriers, and therefore have a lesser chance of collapsing over the enclosed pocket to thereby hinder bone regeneration, but as noted above, require a removal operation. The resorbable barriers have the obvious advantage of not requiring a second operation, but often either have less structural integrity than non-resorbable barriers or have additional support elements, or are otherwise of a stiff construction, that make more difficult precise shaping of the barrier to fit the defect site.

SUMMARY OF THE INVENTION

Briefly stated, the present invention is a bioresorbable barrier for use in the regeneration of bone and/or tissue in either a bone void or a tissue deficiency. In a primary embodiment, the present invention comprises a barrier for use in regeneration of a periodontal bone and/or tissue in a gingival pocket either adjacent to a patient's tooth or in an edentulous area. The barrier includes a formable membrane constructed of a bioresorbable material and having a microstructure configured for aiding and guiding periodontal bone and tissue growth. An activatible bioresorbable hardening agent is impregnated within the membrane. The membrane is formed to a desired shape and the hardening agent is activated so that the membrane retains the desired shape.

In a second aspect, the present invention provides a method of assisting and guiding periodontal bone and/or tissue regeneration in a gingival pocket either adjacent to a patient's tooth or in an edentulous area. The method includes the steps of providing a periodontal barrier as described above, implanting the periodontal barrier about the gingival pocket, forming the membrane into a desired shape which encloses the gingival pocket, and allowing the periodontal bone and/or the periodontal tissue to regenerate into a regeneration space encompassed by the enclosed gingival pocket.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings, which are diagrammatic, embodiments which are presently preferred. It should be understood, however, that the invention is not limited to the precise arrangements and instrumentalities shown. In the drawings:

FIGS. 4A–4E are top plan views of examples of preformed periodontal barriers according to the present invention.

DETAILED DESCRIPTION OF PREFERRED EMBODIMENTS

Certain terminology is used in the following description for convenience only and is not limiting. The words "inner" and "outer" refer to directions toward and away from, respectively, the center of an enclosed periodontal defect. The terminology includes the words above specifically mentioned, derivatives thereof and words of similar import.

Figure 1:
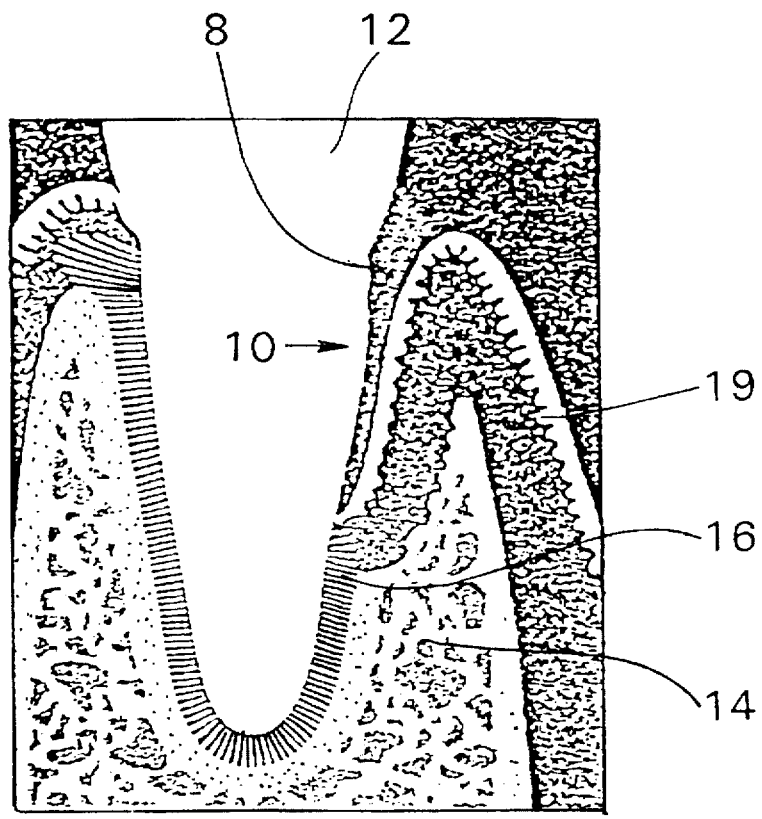
FIG. 1 is a cross-sectional view of a periodontal defect located adjacent to a tooth.

Referring to FIG. 1, there is shown a diagrammatic illustration of a periodontal defect 10 adjacent to a patient's tooth 12 created by the deterioration of periodontal bone 14 and periodontal tissue 16 which has formed a gingival pocket 18 adjacent to the tooth 12 into which the gingiva 19 has migrated. Referring now to FIGS. 2, 3 and 4A–4E, there are shown diagrammatic illustrations of a periodontal barrier 20 for use in regeneration of periodontal bone 14 and/or periodontal tissue 16 in a gingival pocket 18 either adjacent to a patient's tooth 12 or in an edentulous area (not shown), such as an area where a tooth has been extracted. The periodontal barrier 20 is generally comprised of a formable membrane 22 and a hardening agent 24 impregnated within the membrane 22. The membrane 22 is formable to a desired shape and the hardening agent 24 is activatible, to function as described below, so that the membrane 22 retains the desired shape and is prevented from collapsing into the gingival pocket 18.

Referring to FIGS. 2, 3 and 4A–4E, the membrane 22 is preferably constructed of a bioresorbable material and has a microstructure configured for aiding and guiding the growth of periodontal bone 14 and periodontal tissue 16 adjacent to a tooth 12 or in an edentulous area (not shown). Preferably, the membrane 22 includes a beaded rim 23 which provides a smoothed edge to collar the crown-root junction 25 of the tooth 12 when the barrier 20 is implanted. However, it will be recognized by those skilled in the art from the present disclosure that the beaded rim 23 can be omitted, if desired. The membrane 22 is preferably constructed as a thin, pliable sheet of material that is permeable through a plurality of spaced apart pores 26, which are preferably micropores, that are sized so that periodontal bone 14 or tissue 16 is permitted to grow into the interior surface 28 of the barrier 20. In this manner, the barrier 20 acts as a scaffold for bone 14 and tissue 16 formation. Furthermore, the pores 26 are also sized so that the gingiva 19 is permitted to grow into the exterior surface 30 in a manner such that it does not pass through to the interior surface 28 and interfere with the growth of new periodontal bone/tissue but still attaches to the barrier 20 to prevent further apical migration of the gingiva 19. Furthermore, the pores 26 are sized to enable essential nutrients and other necessary materials to pass through the membrane 22 to reach the regenerating periodontal bone 14 and periodontal tissue 16.

Figure 2:
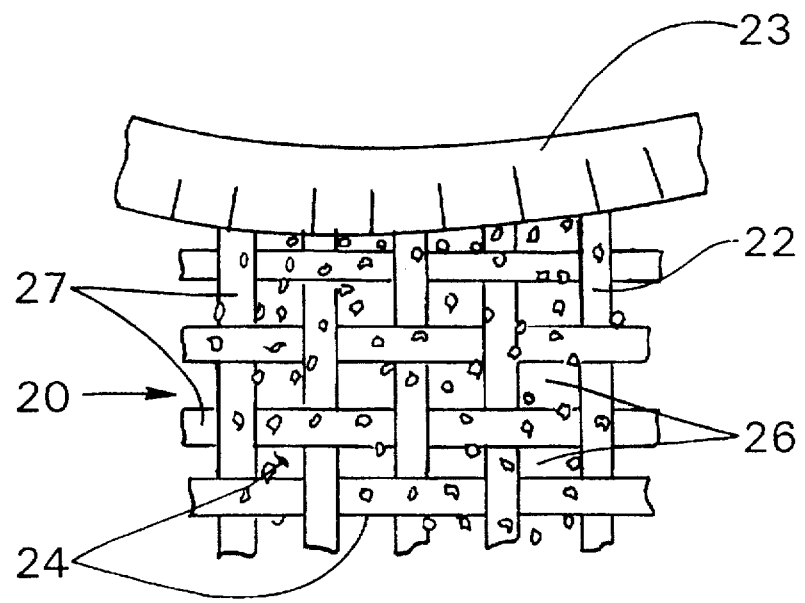
FIG. 2 is a greatly enlarged and exaggerated partial front view of a periodontal barrier according to the present invention, showing the hardening agent as representative particles.

Preferably, the membrane 22 is constructed as a mesh of woven fibers 27 and the pores 26 are the spaces between the woven fibers 27, as shown in FIG. 2. However, it is within the scope of the present invention to construct the membrane 22 as an integral structure such as an open cell sponge-like material or other porous sheet (not shown) in which the pores 26 are through holes formed in the material of the membrane 22.

The hardening agent 24 is impregnated in the material of the membrane 22 by known manufacturing processes. The hardening agent 24 is activatible to transform from an initial state in which the hardening agent 24 does not significantly interfere with the formability of the membrane 22 into a final state in which the hardening agent 24 substantially maintains the membrane 22 as a generally rigid structure. There are two concerns which limit the selection of a suitable material for the hardening agent 24. First, if the hardening agent 24 transforms too rapidly, the membrane 22 would become rigid before being formed to a desired shape for bone 14 and/or tissue 16 regeneration. Second, if the hardening agent 24 transforms too slowly and a prolonged period elapses before the membrane 22 becomes rigid, the barrier 20 may collapse or become distorted from the desired shape due to pressure from sutures or swelling, or contact from the tongue. Therefore, the hardening agent 24 is selected from among materials which provide a sufficient period of time after activation for implantation and forming of the periodontal barrier 20 and thereafter reaches a final state in a short period of time to rigidly maintain the formed shape of the membrane 22 of the barrier 20.

Preferably, the membrane 22 is constructed from commercially available material such as "VICRYL™" mesh, from Johnson & Johnson, Inc., which is a mesh woven from strands of a polygalactin material. However, it is within the scope of the present invention to utilize other suitable materials, such as "GUIDOR" Matrix Barrier available from the John O. Butler Co., or any other appropriate material which is capable of constructing a membrane 22 which would function as described above.

The hardening agent 24 is preferably a medical grade of a calcium sulfate compound, commonly known as plaster of paris, which is bioresorbable. However, it is within the scope of the present invention to utilize any other bioresorbable hardening agent 24 which is capable of being impregnated in the membrane 22 and can be activated to rigidly maintain a formed membrane 22 as described above. In the preferred embodiment, the plaster of paris hardening agent 24 is activated by moistening the barrier 20 with a suitable liquid such as water, sterile water, saline or the like. An alternative embodiment using another material for the hardening agent 24 would utilize other suitable materials to transform the hardening agent 24 from an initial state to a final state as described above. For example, a heat, infrared light or ultraviolet light activated hardening agent could be used.

Figure 3:
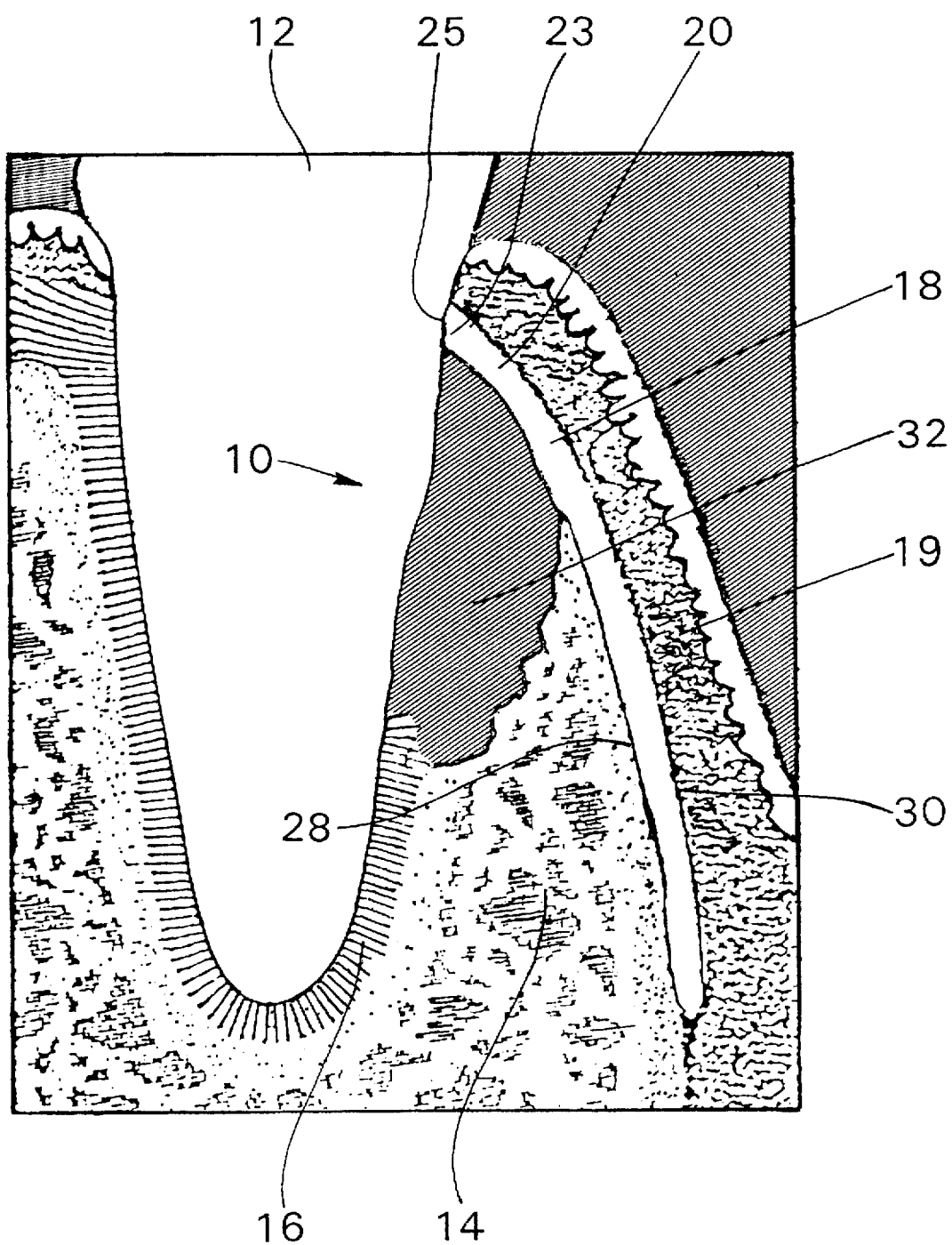
FIG. 3 is a cross-sectional view illustrating a periodontal barrier of the type shown in FIG. 2 implanted about the periodontal defect and enclosing the gingival pocket.

Referring to FIG. 3; there is diagrammatically illustrated an embodiment of a periodontal barrier 20 surgically positioned adjacent to a tooth 12 in accordance with the following method of assisting and guiding periodontal bone 14 and/or periodontal tissue 16 regeneration. The periodontal barrier 20 of the invention is positioned over a gingival pocket 18 adjacent a patient's tooth 12 or in an edentulous area in accordance with the following steps. First, a periodontal barrier 20 as described above is provided as a pre-formed shape or is cut to size and shaped to cover a specific defect site. The hardening agent 24 of the barrier 20 is activated, preferably by moistening the periodontal barrier 20 with a liquid such as water. Next, the periodontal barrier 20 is implanted about either a gingival pocket 18 adjacent to the patient's tooth 12 or an edentulous area. The membrane 22 is then formed into a desired shape which encloses the gingival pocket 18 either adjacent to the patient's tooth 12 or the edentulous area to form a regeneration space 32. The regeneration space 32 encloses the periodontal defect 10, which is the dental area from which periodontal bone 14 or periodontal tissue 16 has deteriorated. The formed membrane 22 includes an outer surface 30 which supports the gingiva 19 and prevents the gingiva 19 from collapsing into the regeneration space 32, which would preclude the regeneration of the bone 14 and the tissue 16 and contribute to further deterioration, and an inner surface 28 providing a scaffold-like structure for bone 14 and/or tissue 16 regeneration. Preferably, the periodontal barrier 20 is sutured in place in a manner well known to those skilled in the art. Finally, the periodontal bone 14 and/or the periodontal tissue 16 is allowed to regenerate in the regeneration space 32 encompassed by the gingival pocket 18. Thereafter, the barrier 20 is absorbed leaving healthy tissue and/or bone. As the preferred embodiment of the periodontal barrier 20 of the present invention is constructed of bioresorbable materials, a subsequent operation to remove the barrier 20 is not required.

The hardening agent 24 is preferably activated prior to implantation of the periodontal barrier 20. However, it is within the scope of the present invention to implant the barrier 20 and then activate the hardening agent 24, either before or after a final forming of the membrane 22 to a desired shape.

Referring to FIGS. 4A–4E, the periodontal barrier 20 of the present invention can be provided pre-cut into one of the illustrated configurations. The particular configurations illustrated are merely exemplary and it is within the scope of the present invention to provide a periodontal barrier 20 pre-cut to any other desired configuration. Furthermore, it is within the scope of the present invention to provide a sheet of material comprised of the porous membrane 22 having the hardening agent 24 impregnated therein, as described above, from which a particular periodontal barrier 20 to be implanted is cut to a desired size and configuration. In any case, the specific configuration and size of the periodontal barrier 10 which is used for a particular application will depend on the size and configuration of the tooth 12 or the edentulous area, the periodontal defect 10 and the growth that is desired.

One particular application of the periodontal barrier 20 of the present invention is to regenerate periodontal bone 14 and/or periodontal tissue 16 in a gap or gaps about a dental implant (not shown). Often, a dental implant is smaller than the extraction socket into which it is placed, which results in gaps about the perimeter of the implant. The periodontal barrier 20 of the present invention is formed and implanted according to the method described above to regenerate periodontal bone 14 and/or periodontal tissue 16 about the dental implant to fill in these gaps.

The periodontal barrier 20 of the present invention is advantageous compared to prior art periodontal barriers. The periodontal barrier 20 is easily formable to enable precise shaping of the membrane 22 during implantation and subsequently becomes a rigid structure which maintains the formed shape and will not collapse into the regeneration space 32 encompassed by the enclosed gingival pocket 18. The barrier 20 achieves the necessary degree of rigidity without non-resorbable struts or supports and without sacrificing formability. Furthermore, the periodontal barrier 20 of the present invention is constructed of bioresorbable materials, so that a second operation is not required to remove the barrier after the periodontal bone 14 and the periodontal tissue 16 have regenerated into the regeneration space 32 encompassed by the enclosed gingival pocket 18.

It will be appreciated by those skilled in the art that the barrier 20 of the present invention can be used for assisting and guiding the regeneration of bone and/or tissue in a bone void and/or a tissue deficiency in body areas other than the dental region. The particular size and shape of such a device would depend on the size and shape of the particular bone void and/or tissue deficiency. The present invention is intended to embrace all such devices which are substantially identically constructed as the barrier 20 of the present invention and the attendant uses of such devices.

It will also be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A bioresorbable barrier for use in regeneration of at least one of periodontal bone and tissue in a gingival pocket being one of adjacent to a patient's tooth and in an edentulous area, said barrier comprising:

a formable membrane constructed of a bioresorbable material and having a microstructure configured for aiding and guiding periodontal bone and periodontal tissue growth, wherein said membrane comprises a woven mesh including strands; and an activatible bioresorbable hardening agent impregnated within said membrane, said hardening agent being activated to hold said membrane in a desired shape.

2. The barrier as recited in claim 1, wherein said hardening agent is plaster.

3. The barrier as recited in claim 1, wherein and said hardening agent is activated by moistening said barrier with water.

4. The barrier as recited in claim 1, wherein said desired shape encloses a regeneration space and said hardening agent prevents said membrane from collapsing into said regeneration space.

5. The barrier as recited in claim 1, wherein said barrier is pre-formed into one of a plurality of shapes and sizes.

6. The bioresorbable barrier as recited in claim 1, wherein said membrane further comprises a beaded rim.

7. A method of assisting and guiding at least one of periodontal bone and tissue regeneration in a gingival pocket being one of adjacent to a patient's tooth and in an edentulous area, comprising the steps of:

providing a barrier comprising a formable membrane constructed of a bioresorbable material and having a microstructure configured for aiding and guiding periodontal bone and periodontal tissue growth, wherein said membrane comprises a woven mesh including strands, and an activatible bioresorbable hardening agent impregnated within said membrane;

implanting said barrier about said gingival pocket;

forming said membrane into a desired shape which covers said gingival pocket; and allowing at least one of said periodontal bone and said periodontal tissue to regenerate into said enclosed gingival pocket.

8. The method as recited in claim 7, further including the step of activating said hardening agent to maintain said desired shape of said membrane.

9. The method as recited in claim 8, wherein said hardening agent is plaster and said step of activating said hardening agent includes moistening said barrier with water.

10. The method as recited in claim 7, wherein said step of forming said membrane includes forming a regeneration space encompassed by said gingival pocket and a support surface to prevent gingiva from collapsing into said regeneration space.

11. A bioresorbable device for use in regeneration of at least one of bone and tissue in one of a bone void and a tissue deficiency, said barrier comprising:

a formable membrane constructed of a bioresorbable material and having a microstructure configured for aiding and guiding bone and tissue growth, wherein said membrane comprises a woven mesh including strands; and an activatible bioresorbable hardening agent impregnated within said membrane, said hardening agent being activated to hold said membrane in a desired shape.

* * * * *